United States Patent
Ryu et al.

(10) Patent No.: US 6,609,024 B1
(45) Date of Patent: Aug. 19, 2003

(54) METHOD OF MAKING A JUDGMENT ON EMOTIONAL POSITIVITY OR NEGATIVITY BY DETECTING ASYMMETRY OF BRAIN WAVES OF LEFT AND RIGHT CEREBRAL HEMISPHERES

(75) Inventors: Chang-Su Ryu, Taejon (KR); Yoon-Seon Song, Taejon (KR)

(73) Assignee: Electronics and Telecommunications Research Institute (KR)

( * ) Notice: Subject to any disclaimer, the term of this patent is extended or adjusted under 35 U.S.C. 154(b) by 0 days.

(21) Appl. No.: 09/417,978

(22) Filed: Oct. 13, 1999

(30) Foreign Application Priority Data

Nov. 12, 1998 (KR) ........................ 1998-48477

(51) Int. Cl.[7] ................................ A61B 5/04
(52) U.S. Cl. ........................ 600/544; 128/925
(58) Field of Search ................ 600/544, 545; 128/925, 924

(56) References Cited

U.S. PATENT DOCUMENTS

| | | | | |
|---|---|---|---|---|
| 4,417,592 A | * | 11/1983 | John | 600/544 |
| 5,083,571 A | * | 1/1992 | Prichep | 600/544 |
| 5,280,793 A | * | 1/1994 | Rosenfeld | 600/545 |
| 5,450,855 A | | 9/1995 | Rosefeld | |
| 5,601,090 A | | 2/1997 | Musha | |
| 5,649,061 A | | 7/1997 | Smyth | |

OTHER PUBLICATIONS

"Estimating Alertness from the EEG Power Spectrum" by T Jung 1997 IEEE pp. 60–69.
A New Mode of Communication Between Man and His Surroundings by Z. Keirn, IEEE vol. 37, No. 12, pp. 1209–1214.
Frontal Brain Asymmetry and Emotional Reactivity: A Biological Substrate of Affective Style by R. Wheeler pp. 82–89.

* cited by examiner

Primary Examiner—Cary O'Connor
Assistant Examiner—Navin Natnithithadha
(74) Attorney, Agent, or Firm—Blakely Sokoloff Taylor & Zafman

(57) ABSTRACT

A method of making a judgment on emotional positivist or negativity of a person, comprises the steps of obtaining asymmetry ratio between the brain waves of the left and right cerebral hemisphere measured in a given unit time by means of electrodes attached to the left and right side of the scalp, calculating asymmetry ratio versus time at each frequency of the measured brain waves if the time taken for measuring the brain waves exceeds a given time interval, calculating an increase and a decrease of the asymmetry ratio of the previous step with time, and entering the increase and decrease into an artificial neural network to make a judgment on the emotional positivity or negativity.

8 Claims, 2 Drawing Sheets

Figure 1:
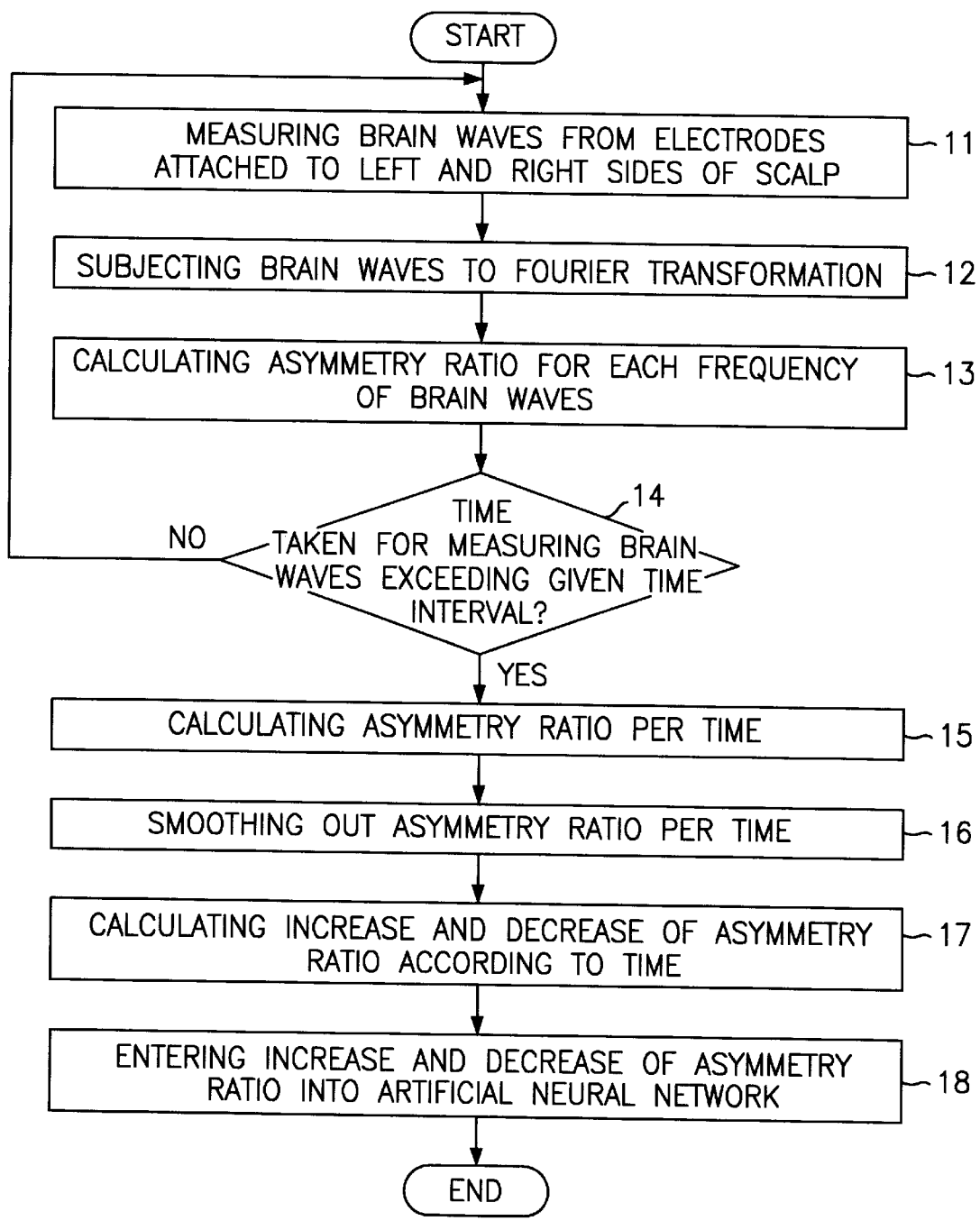

METHOD OF MAKING A JUDGMENT ON EMOTIONAL POSITIVITY OR NEGATIVITY BY DETECTING ASYMMETRY OF BRAIN WAVES OF LEFT AND RIGHT CEREBRAL HEMISPHERES

BACKGROUND OF THE INVENTION

1. Field of the Invention

The present invention concerns a method of making a judgment on emotional positivist or negativity by detecting asymmetry of brain waves of left and right cerebral hemispheres, and a storage medium for storing a computer program to execute such method.

2. Technical Background

Electroencephalography is a technique for recording and interpreting the electrical activity of the brain. The nerve cells of the brain generate electrical signals that fluctuate rhythmically in distinct patterns. These brain-wave patterns are measured and recorded by an instrument called an electroencephalograph, and the recording produced by such an instrument is called an electroencephalogram, commonly abbreviated EEG. To measure the EEG, electrodes are placed on the scalp. Each electrode transmits a signal to one of several recording channels of the electroencephalograph. This signal consists of the difference in the voltage between the electrode and a reference electrode. Electroencephalograph provides a means of studying how the brain works and of tracing correlation between one part of the central nervous system and another. Besides, biofeedback training with brain waves has also been useful in enhancing mental functioning. "Alpha (wave) training" elicits the calming and integrative effects of meditation. Theta wave training has led to more focused attention, the control of "mental blocks" during examinations, and the control of anxiety.

Recently, there has been developed a human-computer interface (hereinafter simply referred to as "interface") that employs brain waves to operate a computer without operating keyboard. Such conventional interface requires the user to be trained to generate particular kinds of brain waves such as alpha wave or asymmetrical waves between the left and right cerebral hemispheres. In order to make a judgment on the psychological state of the user, the data of the brain waves are fully detected throughout the reaction time, for example 10 to 30 seconds, so that the interface is too slow to effectively operate the computer. In addition, a plurality of electrodes must be attached to the scalp, thus making the user inconvenient.

SUMMARY OF THE INVENTION

It is an object of the present invention to provide a method of making a judgment on emotional positivist or negativity of a person without any preparatory training of the person, and a storage medium for storing a program for executing such method.

According to an aspect of the present invention, a method of making a judgment on emotional positivist or negativity of a person comprises the steps of obtaining asymmetry ratio between the brain waves of the left and right cerebral hemispheres measured in a given unit time by means of electrodes attached to the left and right side of the scalp, calculating asymmetry ratio versus time at each frequency of the measured brain waves if the time taken for measuring the brain waves exceeds a given time interval, calculating a change rate of the asymmetry ratio of the previous step with time, and entering the change rate into an artificial neural network to make a judgment on the emotional positivity or negativity.

According to another aspect of the present invention, there is provided a computer storage medium for storing a computer program executed by a computer, wherein the computer program is composed of performing the functions of obtaining asymmetry ratio between the brain waves of the left and right cerebral hemisphere measured in a given unit time by means of electrodes attached to the left and right side of the scalp, calculating asymmetry ratio versus time at each frequency of the measured brain waves if the time taken for measuring the brain waves exceeds a given time interval, calculating a change rate of the asymmetry ratio of the previous step with time, and entering the change rate into an artificial neural network to make a judgment on the emotional positivity or negativity.

The present invention will now be described more specifically with reference to the drawings attached only by way of examples.

BRIEF DESCRIPTION OF THE ATTACHED DRAWINGS

Figure 2:
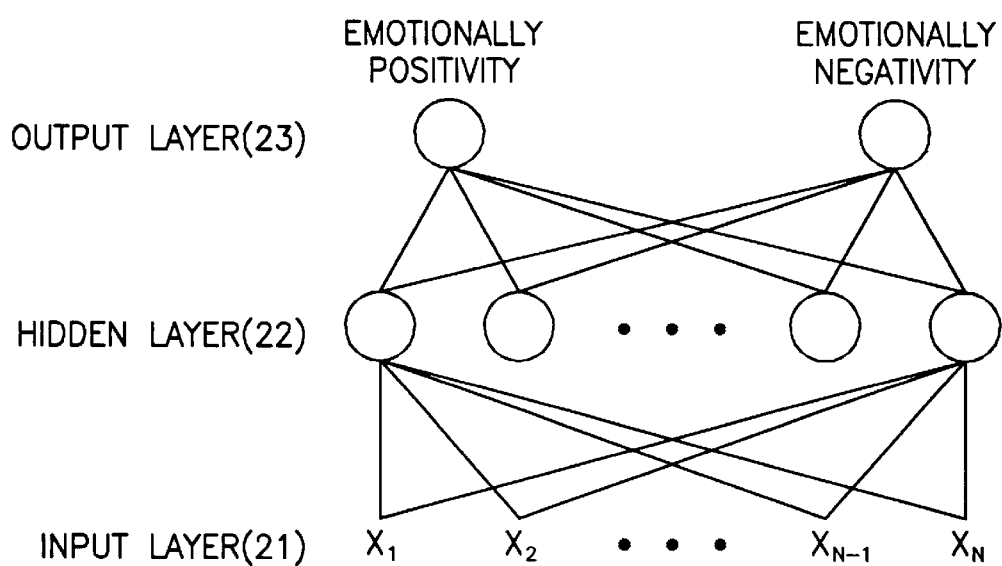

FIG. 1 is a flow chart for illustrating a method of making a judgment on emotional positivity or negativity of a person by detecting asymmetry of brain waves of left and right cerebral hemispheres according to the present invention; and FIG. 2 is a schematic diagram for illustrating the structure and operation of the neural network used for the present invention.

DETAILED DESCRIPTION OF PREFERRED EMBODIMENTS

Referring to FIG. 1, in step 11, brain waves are measured from a pair of electrodes respectively attached to the right and left sides of the scalp. According to 10–20 international electrode system, the left side electrode is placed at position F3 and the right side electrode at F4. The brain waves measured for a given unit time are subjected to the fast Fourier transformation in step 12. Then obtained for each frequency is an output which is the sum of the squared real and imaginary values produced from the fast Fourier transformation. Respectively representing the outputs from the left and right cerebral hemispheres by L and R, the asymmetry ratio between the brain waves of the left and right cerebral hemispheres is defined as $A=(L-R)/(L+R)$ in step 13, where A is an index for the asymmetry of the brain activities of the left and right hemispheres. Of course, such index may be defined in various ways to suitably meet the present invention. In addition, the frequency for obtaining the asymmetry ratio may be in the range of 4 to 30 Hz, which does not limit the application of the present invention.

In step 14, it is determined whether the sum of given unit times taken for measuring the brain waves exceeds a given time interval, which may be defined as 1.024 seconds but adjusted according to the accuracy and promptness of the determination. If not exceeding the given time interval, the steps 11, 12, 13 are repeated. The window used for the fast Fourier transformation may be overlapped with time, having a size of 0.512 second and an overlapping of 75% in the present embodiment. However, the size and overlapping of the widow may be adjusted according to the accuracy and promptness of the determination. On the contrary, if exceeding the given time interval, the asymmetry ratio versus time is calculated at each frequency in step 15.

Subsequently, in step 16, the asymmetry ratio per time calculated in step 15 is smoothed by means of averaging with adjacent data in order to reduce fluctuations in a short time not concerned with the emotional response. Of course, other method may be employed to smooth it in stead of averaging with adjacent data. The smoothed asymmetry ratio obtained in step 16 is again analyzed in step 17 to calculate the slope of an increase or a decrease by employing the method of least square fit. The time interval taken for obtaining the slope is 1.024 seconds in the present embodiment, but may be adjusted according to the accuracy and promptness of the determination. The value or the, positive or negative sign of the slope is entered into the artificial neural network to make a judgment on the emotional positivity or negativity in step 18. When the input value is the positive or negative sign, a suitable threshold value is introduced to make the slopes of small values little concerned with the emotional reaction zero.

Referring to FIG. 2, the neural network comprises multi-layer perceptrons constituting an input layer 21, a hidden layer 22, and an output layer 23. Used as input data are the parameters $X_1, X_2, \ldots X_{N-1}, X_N$ (subscripts represent frequencies used) of an increase and a decrease of the asymmetry ratio at each frequency. In this case, the parameters for frequencies below 4 Hz affected by artifacts such as movement of eye balls are excluded while those for theta wave of 4 to 7 Hz, alpha wave of 8 to 13 Hz and beta wave of 14 to 30 Hz concerned with emotional information are employed. Of course, other frequency bands may be employed to input the parameters of an increase rise and a decrease of the asymmetry ratio. Thus, the output of the neural network is the emotional positivity or negativity, and the learning process of the neural network achieved by algorithm of the conventional error back-propagation. The input data consisting of parameters of increase and decrease of the asymmetry ratio at each frequency is used for the learning process of the neural network. Having completed the learning process, the neural network makes a judgment on emotional positivity or negativity based on the input data.

Thus, the inventive interface enables the user to directly communicate with the computer by means of brain waves without any other learning process to generate particular brain waves. In addition, the increase and decrease of the asymmetry ratio versus time between the left and right brain waves are obtained by analyzing the brain-wave data of about 1 second, thereby providing a real time interface. Further, the pair of electrodes respectively attached to the left and right sides of the scalp may be used in the form of a head band.

While the present invention has been described in connection with specific embodiments accompanied by the attached drawings, it will be so appreciated by those skilled in the art that various changes and modifications may be made thereto without departing the gist of the invention.

What is claimed is:

1. A method of making a judgment on emotional positivity or negativity of a person, comprising the steps of:

obtaining asymmetry ratio between the brain waves of the left and right cerebral hemisphere measured in a given unit time by means of electrodes attached to the left and right side of the scalp;

calculating asymmetry ratio versus time at each frequency of said measured brain waves if the time taken for measuring said brain waves exceeds a given time interval;

calculating a slope of the asymmetry ratio of the previous step with time; and entering a sign of said slope into an artificial neural network to make a judgment on said emotional positivist or negativity.

2. A method as defined in claim 1, wherein the first step includes further steps of:

measuring said brain waves from said electrodes; subjecting said brain waves to Fourier transformation; and obtaining said asymmetry ratio between the left and right brain waves based on the previous Fourier transformation.

3. A method as defined in claim 1, wherein the second step includes further steps of:

performing the first step if the time taken for measuring said brain waves does not exceed said given time interval; and calculating asymmetry ratio versus time at each frequency of said measured brain waves if the time taken for measuring said brain waves exceeds a given time interval.

4. A method as defined in claim 2, wherein said electrodes are two respectively attached to the left and right sides of the scalp with the left side one positioned at F3 and the right side one at F4 according to 10–20 international electrode system.

5. A method as defined in one of the claims 1 to 4, wherein the third step includes further steps of:

smoothing out said asymmetry ratio versus time; and calculating an increase and a decrease of the smoothed asymmetry ratio with time.

6. A method as defined in claim 5, wherein the step of smoothing out said asymmetry ratio is to reduce fluctuations for a short time little concerned with emotional response.

7. A method as defined in claim 5, wherein said an increase and a decrease is the slope of said asymmetry ratio with time or the positive or negative sign of said slope.

8. A computer storage medium for storing a computer program executed by a computer, wherein said computer program is composed of performing the functions of obtaining asymmetry ratio between the brain waves of the left and right cerebral hemisphere measured in a given unit time by means of electrodes attached to the left and right side of the scalp;

calculating asymmetry ratio versus time at each frequency of said measured brain waves if the time taken for measuring said brain waves exceeds a given time interval;

calculating an increase and a decrease of the asymmetry ratio of the previous step with time; and entering said an increase and a decrease into an artificial neural network to make a judgment on said emotional positivity or negativity.

\* \* \* \* \*